United States Patent [19]

Martin

[11] Patent Number: 4,908,469

[45] Date of Patent: Mar. 13, 1990

[54] 2-HYDROXY-PROPANOIC ACID ACYCLIC ALKYL ESTERS FOR BENZOTHIAZEPINES

[75] Inventor: Daniel E. Martin, Lee's Summit, Mo.

[73] Assignee: Marion Laboratories, Inc., Kansas City, Mo.

[21] Appl. No.: 195,709

[22] Filed: May 18, 1988

[51] Int. Cl.$^4$ ............................................ C07C 149/40
[52] U.S. Cl. ....................................... 560/17; 562/431; 549/549; 540/491
[58] Field of Search .................... 540/491; 549/549; 560/17; 562/431

[56] References Cited

U.S. PATENT DOCUMENTS

| | | | |
|---|---|---|---|
| 3,562,257 | 2/1971 | Kugita et al. | 540/491 |
| 4,416,819 | 11/1983 | Nagao et al. | 540/491 |
| 4,420,628 | 12/1983 | Inoue et al. | 560/17 |
| 4,533,748 | 8/1985 | Manghishi et al. | 540/491 |
| 4,552,695 | 11/1985 | Igarashi et al. | 540/491 |
| 4,567,175 | 1/1986 | Takeda et al. | 540/491 |

FOREIGN PATENT DOCUMENTS

| | | | |
|---|---|---|---|
| 0338893 | 10/1989 | European Pat. Off. | 560/17 |
| 60-013775 | 1/1985 | Japan | 560/17 |
| 60-013776 | 1/1985 | Japan | 560/17 |
| 60-78973 | 5/1985 | Japan | 540/491 |
| 61-268663 | 11/1986 | Japan | 560/17 |

OTHER PUBLICATIONS

Sharpless et al., *J. Am. Chem. Soc.*, 102, 5974–5976 (1980).

*Primary Examiner*—Robert T. Bond
*Attorney, Agent, or Firm*—Christopher John Rudy

[57] ABSTRACT

In general, the present invention provides, in one aspect, a process comprising contacting a 2-Aminothiophenol with an optically active 3-(4-alkyloxyphenyl)glycidic acid acyclic alkyl ester by step(s) under conditions such that an optically active 2-hydroxy-3-(4-alkyloxyphenyl)-3-(2-Aminophenylthio)propionic acid acyclic alkyl ester is prepared. Another aspect comprises the optically active 2-hydroxy-3-(4-alkyloxyphenyl)-3-(2-Aminophenylthio)propionic acid acyclic alkyl ester. A preferred aspect is a process comprising contacting 2-aminothiophenol per se with a 3-(4-methoxyphenyl)glycidic acid methyl ester by step(s) under conditions such that a 2-hydroxy-3-(4-methoxyphenyl)-3-(2-aminophenylthio)propionic acid methyl ester is prepared.

14 Claims, No Drawings

2-HYDROXY-PROPANOIC ACID ACYCLIC ALKYL ESTERS FOR BENZOTHIAZEPINES

FIELD

This invention concerns benzothiazepines and such precursors therefor as those including 3-(4-alkoxyphenyl)-3-(aminophenylthio)propionic acid esters, and so forth and the like, with a process therefor which employs aminothiophenols and the like. The benzothiazepines are useful central depressants, tranquilizers, antihypertensives, vasodilators and angiotensin converting enzyme inhibitors and intermediates for the manufacture of other drugs and agricultural chemicals.

BACKGROUND

Kugita et al., U.S. Pat. No. 3,562,257 (Feb. 9, 1971), describes benzothiazepine derivatives, which are useful as antidepressants, tranquilizers and coronary vasodilators. Among these, diltiazem, i.e., 3-(acetyloxy)-5-[2-(dimethylamino)ethyl]-2,3-dihydro-2-(4-methoxyphenyl)-1,5-benzothiazepin-4(5H)-one, is a well-known successful cardiac drug having calcium blocking activity. Vasodilating action is specific for the d-cis-isomer, (+)-cis-5-[2-dimethylamino)ethyl]-2,3-dihydro-3-hydroxy-2-(p-methoxyphenyl)-1,5-benzothiazepin-4(5H)-one acetate (ester). The hydrochloride is often administered as, e.g., Cardizem®. Other 1,5-benzothiazepine derivatives are useful hypotensive agents and/or coronary or cerebral vasodilators and are known to have desired or enhanced effects from a select optical isomer as well. For example, (+)-cis-5-[2-dimethylamino)ethyl]-2,3-dihydro-3-acetoxy-2-(4-methoxyphenyl)-8-chloro-benzothiazepin-4(5H)-one and its pharmaceutically acceptable salt(s), etc. fit this category. See e.g., Takeda et al., U.S. Pat. No. 4,567.175 (Jan. 28, 1986). Further useful benzothiazepines are known as well. See e.g., present U.S. Pat. class 540 subclass 491, etc.

As might be expected, various processes or methods for preparing such benzothiazepines are generally further known. In order to isolate the desired optically active isomer such methods may typically include at least one resolution step.

Nagao et al., U.S. Pat. No. 4,416,819 (Nov. 22, 1983), describes a process for preparing 1,5-benzothiazepine derivatives. In preparing a racemic 2-hydroxy-3-(lower alkoxyphenyl)-3-(2-aminophenylthio)propionic acid used in that process, a 3-(lower alkoxyphenyl)glycidic acid ester is condensed with a 2-aminothiophenol in order to produce a 2-hydroxy-3-(lower alkoxyphenyl)-3-(2-aminophenylthio)propionic acid ester, which is hydrolyzed in order to produce the corresponding propionic acid intended to be employed in the process. That process is one which would employ a subsequent optical resolution step in order to isolate the desired optically active isomer as well.

Shimada et al., Jpn Koliai Tokkyo Koho Disclosure No. 78973-1985 (May 4, 1985), purportedly describes a method of producing 1,5-benzothiazepine derivatives. A racemic 3-(4-lower alkyoxyphenyl)glycidic acid lower alkyl ester is condensed with 2-aminothiophenol under neat conditions.

Sandada et al., Jpn. Discl. No. 268663-1988 (Nov. 28, 1986), discloses a method of producing optically active 2-hydroxy-3,3-di-substitued-propionic acid. Therein, a (2R,3S)-2,3-epoxy-3-(4-lower-alkoxyphenyl)propionic acid (−)menthyl ester purportedly is allowed to react with 2-aminothiophenol to produce 2(S)-hydroxy-3(S)-(4-lower-alkyloxyphenyl)-3-(2-aminophenylthio)propionic acid (−)-menthyl ester, followed by hydrolysis, which hydrolyzed acid product may be used to prepare corresponding 1,5-benzothiazepine derivatives, e.g., diltiazem hydrochloride.

In another particular type of method, a step intends condensing a 3-(4-alkyloxyphenyl)glycidic acid ester with a 2-nitrothiophenol in order to prepare a 2-hydroxy-3-(4-alkyloxyphenyl)-3-(2-nitrophenylthio)-propionic acid ester. The starting epoxy esters may be optically active. Such a condensing step generally requires a catalyst or reaction accelerator, and these types of methods require a further step of reducing the aromatic nitro group to an amino in order to obtain the desired benzothiazepines. See e.g., Inoue et al., U.S. Pat. No. 4,420,628 (Dec. 13, 1983); Sawai et al., Jpn. Kokai Tokkyo Kojo No. 60-13775 (Jan. 24, 1985); Sawai et al., Jpn. Kokai Tokkyo Kojo No. 60-13776 (Jan. 24, 1985).

Ingarashi et al., U.S. Pat. No. 4,552,695 (Nov 12, 1985), describes a process for production of diltiazem hydrochloride. Steps in that 10-step process include employing an optically active 3-(4-acyloxyphenyl)glycidic acid ester, which is converted to a chlorohydrin. The chlorohydrin is allowed to react with an orthonitrothiophenol to obtain a 2-hydroxy-3-(4-acyloxyphenyl)-3-(2-nitrophenylthio)propionic acid ester. Subsequent steps include protecting the 2-hydroxy group, reducing the aromatic 2-nitro group to the 2-amino, and cyclizing, alkylating, acetylating and so forth.

Manghishi et al., U.S. Pat. No. 4,533,748 (Aug. 6, 1985), describes a process for the optical resolution of dl-2-hydroxy-3-(4-methoxyphenyl)-3-(2-aminophenylthio)propionic acid. The resolved (+)$_D$-isomer is an intermediate in the production of diltiazem.

SUMMARY

In general, the present invention provides, in one aspect, a process comprising contacting a 2-Aminothiophenol with an optically active 3-(4-alkyloxyphenyl)glycidic acid acyclic alkyl ester by step(s) under conditions such that an optically active 2-hydroxy-3-(4-alkyloxyphenyl)-3-(2-Aminophenylthio)propionic acid acyclic alkyl ester is prepared. Another aspect comprises the optically active 2-hydroxy-3-(4-alkyloxyphenyl)-3-(2-Aminophenylthio)propionic acid acyclic alkyl ester. A preferred aspect is a process comprising contacting 2-aminothiophenol per se with a 3-(4-methoxyphenyl)glycidic acid methyl ester by step(s) under conditions such that a 2-hydroxy-3-(4-methoxyphenyl)-3-(2-aminophenylthio)propionic acid methyl ester is prepared.

The optically active 2-hydroxy-3-(4-alkyloxyphenyl)-3-(2-Aminophenylthio)propionic acid ayclic alkyl esters are useful intermediates for 1,5-benzothiazepines. Significantly, employing the resolved 3-(4-alkyloxyphenyl)glycidic acid acyclic alkyl este can avoid further resolution at later stages in a process for preparing the 1,5-benzothiazepines, which thus is more efficient in that resolution is carried out earlier in the process and costly resolving agents otherwise used, particularly at the later stages, can be avoided as well. In addition, reduction of a nitro group is avoided. The 2-aminothiophenol per se is readily commercially available and needs no additional processing to be used in this invention, unlike 2-nitrothiophenol and methods employing its use. Also significantly, such an optically active 2- hydroxy-3-(4-alkyloxyphenyl)-3-(2-Aminophenylthio)-propanoic acid acyclic alkyl ester as for example, the 2-hydroxy-3-(4-methoxy-phenyl)-3-(2-aminophenylthio)propanoic acid methyl ester per se, can afford even further processing economics when involved in preparing such a 1,5-benzothiazepine as, for example, diltiazem or its hydrochloride, because it is advantageously readily crystallizable in high yield from such reaction media as, for example, toluene, near ambient temperature.

Illustrative Detail

In general, 2-Aminothiophenols employable in the practice of this invention are aromatic organic compounds having a phenyl or suitably substituted phenyl nucleus or the like, which has an aromatic thiol group or the like and an aromatic amino or suitably substituted amino group bonded to the phenyl nucleus. The upper case "A" in the 2-Aminophenylthio group indicates that the Amino moiety may be primary ($-NH_2$) or suitably substituted, and it also is an indicator of possible ring substitution on the phenyl ring. The 2-Aminothiophenols include those represented by the following general formula (I):

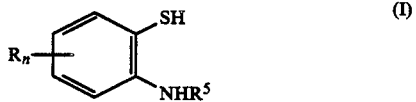

wherein:
n is an integer from 0 to 3, or from 0 to 2, especially 0 or 1;
R is separately at each occurrence halogen, lower alkyl, especially $C_{1-6}$ alkyl or $C_{1-4}$ alkyl lower alkyloxy, lower alkylthio, lower alkanoloxy, hydroxy, benzyloxy, trifluoromethyl, nitro, cyano, or if n is 2 or more, a bridged alkyl, e.g., tri- or tetramethylene, particularly ethyl, methyl, methoxy, $NO_2$, CN, Cl, F, $CF_3$ and
$R^5$ is hydrogen or lower alkyl, especially H or methyl. Examples of the 2-Aminothiophenols thus include 2-aminothiophenol per se (n=0 & $R_5>$=H) and 2-amino-5-chlorothiophenol.

The 2-Aminothiophenols can be obtained, or they can be prepared by generally known methods or by methods analogous thereto. See generally, Kugita et. al., supra, etc.

In general, optically active 3-(4-alkyloxyphenyl)glycidic acid acyclic alkyl esters employable in the practice of this invention are epoxy or the like compounds having a carboxylic acid acyclic alkyl ester group or the like bonded to one carbon of the epoxy ring and such an aromatic group as a 4-alkyloxyphenyl group or the like bonded to the other carbon of the epoxy ring, and which have an optical activity component of net optical activity due to the presence of the two optically active carbons of the epoxy ring. The optically active 3-(4-alkyloxyphenyl)glycidic acid acyclic alkyl esters include those represented by the following general formula (II):

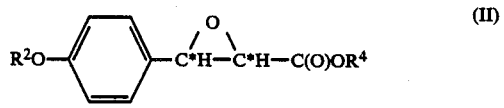

wherein:
$R^2$ is lower alkyl, especially $C_{1-6}$ alkyl, or $C_{1-4}$ alkyl, or methyl and
$R^4$ is acyclic lower alkyl, especially $C_{1-6}$ alkyl, or $C_{1-4}$ alkyl, or methyl and wherein
the optical activity component of net optical activity is due to the presence of the chiral epoxy carbons (C*), especially of the $(-)_{578}$-trans-epoxy isomers. An example of the optically active glycidic acid acyclic alkyl esters thus includes $(-)_{578}$-trans-3-(4-methoxyphenyl)glycidic acid methyl ester.

Optical purity of a sample of the optically active 3-(4-alkyloxyphenyl)glycidic acid acyclic alkyl ester may thus vary within the practice of this invention. The optical purity can be from slight optical activity or just above the optical activity found in a racemic mixture of a 3-(4-alkyloxyphenyl)glycidic acid acyclic alkyl ester sample, with respect to the optical activity due to the chiral epoxy carbons to substantially or even essentially or more optically pure, as with a 100% enantiomerically pure sample. The mentioned racemic mixture is arbitrarily assigned or actually has, a 0% optical purity value. The mentioned racemic mixture may however show optical activity due to chirality on the molecules other than the chiral epoxy carbons, i.e., from a chiral auxillary, and vice versa. The optical purity can be thus, say, 10% or more, 50% or more, 80% or more, 95% or more to include 98% or more and 99% or more. Nonetheless, greater advantages generally attend the employment of optically active 3-(4-alkloxyphenyl)glycidic acid alkyl esters of reasonably high purity in the practice of this invention.

The optically active 3-(4-alkyloxyphenyl)glycidic acid acyclic alkyl esters can be obtained, or they can be prepared by generally known methods or by methods analogous thereto. See generally, Sharpless et al., J. Am. Chem. Soc., 102, 5974–6 (1980); Sawai et al., both supra, etc.

In addition, optically active 3-(4-methoxyphenyl)glycidic acid acyclic alkyl esters can be prepared through optical resolution of a racemic mixture or an optically enriched sample of 3-(4-methoxyphenyl)glycidic acid: Illustratively thus, for example, to an ice-water bath cooled solution of 25.1 g of potassium hydroxide in 378 mL of methanol is added 50.0 g of racemic 3-(4-methoxyphenyl)glycidic acid methyl ester, with stirring. Stirring is continued for 2 hours, and the product is filtered and is washed with cold methanol and next cold acetone and is dried under vacuum at ambient temperature, yielding 54.3 g of the corresponding racemic potassium salt. A 54.0 g sample of this salt is dissolved in 425 mL of an ice-water mixture, and the reaction vessel is cooled with an ice-water bath. A sample of 159 mL of diethyl ether is added, followed by 29.6 g of optically pure (−)-methylbenzylamine. A solution of 22 mL concentrated HCl in 193 mL of water is added dropwise over 20 minutes, and the mixture is stirred for 40 minutes after the completion of the HCl addition. The product is collected and is washed with cold diethyl ether and next cold acetone, and is dried, yielding 29.5 g of the diastereomeric salt. To a NaCl/ice-water bath-cooled solution of 22.4 g KOH in 268 mL of methanol, is added 37.7 g of the (−,−)-methylbenzylamine diastereomeric salt of 3-(4-methoxyphenyl)glycidic acid, $[\alpha]_{578}^{21.5}=-116°$ (0.05008 g/10 mL methanol) which is stirred for 1 hour under a nitrogen blanket, and from which is collected the solid $(-)_{578}$-3-(4-methoxyphenyl)glycidic acid, potassium salt, which is washed with cold methanol and cold acetone and is dried, yielding 24.4 g (88.3% of theory). Next, to a stirred mixture of 10.5 g of this (−)−potassium salt in 51 mL of dimethylformamide (dried over 4 Å molecular sieves) at ambient temperature under a nitrogen blanket, is added all at once 5.0 mL aliquot of ambient temperature dimethylsulfate (Aldrich). After a brief rise in temperature to 32° C., the temperature of the mixture drops back to ambient. Stirring is continued, and after reaching about 4-¾ hours from the addition, the mixture is cooled in an ice-water bath. Next, 51 mL of cold water is added to the mixture over a two-minute period. The aqueous mixture at 5° C. is seeded with a small quantity of (−)$_{578}$-trans-3-(4-methoxyphenyl)glycidic acid methyl ester crystals, causing instant crystallization. Upon waiting 10 minutes, the desired solid is collected by filtration and is dried under vacuum at ambient temperature, which affords 7.58 g of solid. The solid is recrystallized from 80 mL of 82:1 ethanol to water mixture, by volume, which is heated to 65° C. and is next allowed to stand under ambient temperature conditions. Upon passage of 2-¾ hours, the last hour of which is with stirring, solid is collected and is rinsed with ca. 35 mL of ambient temperature 82:1 ethanol to water mixture, yielding 5.16 g (−)$_{578}$-3-(4-methoxyphenyl)glycidic acid methyl ester; $[\alpha]_{578}^{22} = -212.2°$ (0.05041 g/10 mL methanol); m.p.=89.2° C. The product may be stored under refrigeration.

This invention may be practiced with 2-aminothiophenol per se and 3-(4-methoxyphenyl)glycidic acid methyl ester, which may be racemic as well as resolved. However, employment of (−)-trans-3-(4-methoxyphenyl)glycidic acid methyl ester is preferred.

In general, optically active 2-hydroxy-3-(4-alkyloxyphenyl)-3-(2-Aminophenylthio)propionic acid acyclic alkyl esters are propionic acid or the like derivatives having 2-hydroxy, acyclic alkyl ester, 3-(4-alkyloxyphenyl) and 3-(2-Aminophenylthio) groups, or any of their like(s) bonded thereto. The upper case "A" in the "2-Aminophenylthio" indicates that the Amino moiety may be primary (−NH$_2$) or suitably substituted, and is an indication of possible ring substitution on the phenyl ring as well. Optical activity is that component of net optical activity which is due to the mentioned 2- & 3- chiral carbons of the propionic chain. The optically active 2-hydroxy-3-(4-alkyloxyphenyl)-3-(2-Aminophenylthio)propionic acid acyclic alkyl esters include those represented by the following general formula (III):

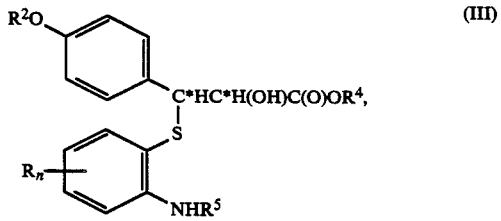

wherein the n, R$^2$, R$^4$, R$^5$ and C* groups or moieties are as in the formulae I & II. Examples of the optically active 2-hydroxy-3-(4-alkyloxyphenyl)-3-(2-Aminophenylthio)propionic acid acyclic alkyl esters thus include (+)$_{578}$,s-(2S,3S)-2-hydroxy-3-(4-methoxyphenyl)-3-(2-aminophenylthio)propionic acid methyl ester and (+)$_{578}$-(2S,3S)-2-hdroxy-3-(4-methoxyphenyl)-3-(2-amino-5-chlorophenylthio)propionic acid methyl ester.

The optically active 2-hydroxy-3-(4-alkyloxyphenyl)-3-(2-Aminophenylthio)propionic acid acyclic alkyl esters of this invention can be prepared by contacting the 2-Aminothiophenol(s) with the optically active 3-(4-alkyloxyphenyl)glycidic acid acyclic alkyl ester(s). Step(s) and conditions are those sufficient to prepare said 2-hydroxy esters.

Amounts of the reactants may vary. For example, suitable molar ratios of the 2-Aminothiophenol(s) to the glycidic acid acyclic alkyl esters include those about from 1:1 to 1.5:1. Preferably, a slight excess of the 2-aminothiophenol(s) is(are) employed, e.g., about a 1.2:1 molar ratio.

Preferably, the 2-hydroxy ester-forming process is carried out in the presence of a suitable medium or suitable media such as a suitable aprotic solvent, which by way of illustration, may be at least one C$_{7-8}$ aromatic hydrocarbon, for example, toluene, o-, m- and/or p-xylene(s), and/or ethylbenzene, and/or at least one C$_{7-8}$ aryl-alkyl ether, for example, anisole, and so forth. Other media may be employed, such as, for example, 1,4-dioxane, tetrahydrofuran, and so forth, or acetonitrile, but the latter is not as desirable because crystallization of the desired 2-hydroxy ester product may not occur therewith. Toluene is an advantageous media. Higher boiling media may also be advantageous in that the process may be accelerated thus at atmospheric pressure due to the greater boiling temperatures.

Concentration of the components in the medium or media may vary. For example, suitable molar concentrations of the epoxide in the media include those about from 0.75 M to 1.5 M, or so. Preferably, about 5 mL of the medium is employed with about 1 g of the epoxide.

Temperatures of the 2-hydroxy ester-forming process are those which are suitably employed. Preferably, suitable temperatures include those about from 60° C. to 150° C., desirably about from 80° C. to 140° C., especially about 100° C. or above, in general.

Pressures of the 2-hydroxy ester-forming process may be subatmospheric to superatmospheric, but are conveniently ambient. Regulation of the pressure may be employed to raise or lower the temperature, for instance, as is known in the art.

Times of the 2-hydroxy ester-forming process can vary, primarily upon the level of completion desired, the temperature and so forth. Times about from an hour or less to a score (20) hours or more may be employed, with times about from two or three to six or seven hours generally more typical.

The 2-hydroxy ester-forming process system may be kept inert. For example, an inert atmosphere and/or an actinic radiation shield may be employed.

The 2-hydroxy ester may be isolated and/or purified by generally known methods. For example, solid ester may be filtered and washed. Decantation, scooping, evaporation and so forth and the like may be employed.

The 2-hydroxy ester is preferably recovered as a solid. Cooling to below ambient temperatures may be employed but may not be necessary, particularly to isolate appropriate solid optically active 2-hydroxy esters.

Surprisingly, the optically pure 2-hydroxy esters can have a significantly less solubility in the medium than the corresponding racemic ester. For example, the following table demonstrates such an unexpectedly advantageous solubility characteristic as illustrated by the following isomeric samples of 2-hydroxy-3-(4-methoxyphenyl)-3-(2-aminophenylthio)propionic acid methyl ester.

| Sample | Solubility in ambient temperature toluene |
|---|---|
| Racemic | 29.4 m/mL |
| (+)$_{578}$—(2S,3S) | 13.7 mg/mL |
| (−)$_{578}$—(2R,3R) | 14.2 mg/mL |

Yields of the propionic acyclic alkyl ester product can be very high. Yields can be in general above about 25, at least 50 or 75 or more percent of theory. Significantly, yields of the optically active propionic acid acyclic alkyl esters are generally higher than with the corresponding racemate.

The 2-hydroxy esters may be employed to prepare corresponding benzothiazepines. Methods known in the art or analogous thereto may be employed, which generally involve cyclization, etc. Additional step(s) to further derivatize the benzothiazepines can thus include: N-alkylation, acetylation or the like, and/or a pharmaceutically acceptable salt, e.g., hydrochloride salt, formation. Methods for these steps are known in the art or are analogous thereto as well. In preparing the benzothiazepines with the optically active 2-hydroxy esters of this invention, further resolution may not be necessary.

The present invention is decidedly advantageous to practice.

The following examples further illustrate this invention.

EXAMPLE 1

To a 25 mL round-bottom flask, which is equipped with a water-cooled reflux condenser, nitrogen atmosphere adapter and magnetic stirrer, is added 1.50 g of (−)$_{578}$-trans-3-(4-methoxyphenyl)glycidic acid methyl ester $[\alpha]_{578}^{22} = -212°$ (0.0504 g/10 mL methanol); m.p.=89.1° C. Next is added 1.04 g of 2-aminothiophenol (Aldrich), and next is added 7.5 mL of toluene (HPLC grade, Baker). The flask, its contents being under a nitrogen blanket, is lowered into an oil bath at 115° C., and magnetic stirring is commenced with reflux condenser being operational. Upon the passage of 5 hours from the immersion into the oil bath, no unreacted epoxide is observed by means of TLC (1:1 by volume ethyl acetate to hexanes), and the flask is removed from the oil bath, stirring being ceased as well, at 5-½ hours from the immersion into the oil bath. Crystallization begins to occur within one hour. The flask and its contents are allowed to stand overnight at ambient temperature under the nitrogen blanket. The solid is collected by filtration and is washed with 10 mL of toluene at ambient temperature. Next, the solid is dried under high vacuum at ambient temperature, yielding 1.92 g of (+)$_{578}$-threo-(2S,3S)-2-hydroxy-3-(4-methoxyphenyl)-3-(2-amino phenylthio)propionic acid methyl ester (80.0 percent of yield from first crop) $[\alpha]_{578}^{24} = +307°$ (0.050 g/10 mL methanol); $[\alpha]_D^{2232} +294°$ (0.050 g/10 mL methanol) m.p. =111.8° C. The product is stored in a freezer.

EXAMPLE 2

The procedure of Example 1 is repeated except using 1.50 g of racemic trans-3-(4-methoxyphenyl)glycidic acid methyl ester. Crystallization begins to occur from about 1 hour to 2-½ hours. The yield of racemic threo-2-hydroxy-3-(4-methoxy-phenyl)-3-(2-aminophenylthio)-propionic ester is 1.63 g (67.9 percent of theoretical); m.p. =93.5° C.

EXAMPLE 3

The procedure of Example 1 is repeated except using 0.50 g of the (−)$_{578}$-trans-3-(4-methoxyphenyl)glycidic acid methyl ester, and scaling down the other materials proportionately. Also, the heating is continued for 6 hours. The yield of solid (+)$_{578}$-threo-(2S,3S)-2-hydroxy-3-(4-methoxyphenyl)-3-(2-aminophenylthio)-propionic acid methyl ester is 0.594 g (74.2 percent of theoretical yield from first crop); $[\alpha]_{578}^{30} = +301°$ (0.050 g/10 mL methanol; m.p.=112.2 ° C.

EXAMPLE 4

The procedure of Example 3 is repeated except using 0.50 g of racemic trans-3-(4-methoxyphenyl)glycidic acid methyl ester. No solid is isolated under these conditions, but cooling the flask contents in an ice-water bath for 15 minutes results in precipitation of 0.548 g of solid product (68.5 percent of theoretical).

EXAMPLE 5

The procedure of Example 1 is repeated except using a 1.50 g sample of 84 percent enantiomerically pure (−)$_{578}$-trans-3-(4-methoxyphenyl)glycidic acid methyl ester, which is prepared by mixing 68 parts by weight of the (−)$_{578}$-trans-3-(4-methoxyphenyl)glycidic acid methyl ester of Example 1 and 32 parts by weight of the corresponding racemic trans-ester. A solid precipitates from the toluene mother liquor between 1-½ and 4 hours and is similarly washed and dried, yielding 1.62 g (67.5 percent of theoretical yield); $[\alpha]_{578}^{24} = +269°$ (0.050 g/10 mL methanol); $[\alpha]_D^{22} = +261°$ (0.050 g/10 mL methanol); (ca. 88 percent optically pure); m.p. =107.4° C.

EXAMPLE 6

The procedure of Example 1 is repeated except using 0.30 g epoxide, and generally scaling for the other components proportionately using 1.5 mL of a mixture of xylenes (Baker) is used in lieu of the toluene. Precipitation occurs within 20 minutes at ambient temperature. Upon cooling in a freezer and isolation, the yield of solid product is 0.326 g (67.9 percent of theoretical yield $[\alpha]_{578}^{24} = +302°$ (0.050 g/10 mL methanol); $[\alpha]_D^{22} = +293°$ (0.050 g/10 mL methanol); m.p.=111.8° C.

EXAMPLE 7

The procedure of Example 6 is repeated except using 0.30 g of racemic trans-3-(4-methoxyphenyl)glycidic acid methyl ester. Precipitation occurs in about 40 minutes at ambient temperature. Upon freezer cooling and isolation, the yield of solid product is 0.240 g (50.0 percent of theoretical yield); m.p. =85.7° C.

EXAMPLE 8

The procedure of Example 3 is repeated except using 2.5 mL of anisole (Aldrich) in lieu of the toluene. The reaction is conducted at 140° C. to 143° C. for 4½ hours. No precipitation occurs even overnight. Cooling in a freezer yields 0.364 g of the solid product (45.5 percent of theoretical yield); $[\alpha]_{578}^{24} = +292°$ (0.050 g/10 mL methanol); $[\alpha]_D^{22} = +282.4°$ (0.0513 g/10 mL methanol); m.p.=108.3° C.

EXAMPLE 9

The procedure of Example 8 is repeated except using racemic trans-3-(4-methoxyphenyl)glycidic acid methyl ester. No precipitation occurs even overnight. Cooling in a freezer yields 0.204 g of the solid product (25.5 percent of theoretical yield); m.p.=88.6° C.

EXAMPLE 10

The product of Example 1 is used to make diltiazem hydrochloride. No further resolutions are needed.

Epilogue

The present invention is thus provided. Various modifications can be effected by those skilled in the art within the spirit of this invention, the scope of which is particularly pointed out by the following distinctly claimed subject matter.

What is claimed is:

1. A process comprising contacting a 2-Aminothiophenol with an optically active 3-(4-alkyloxyphenyl)glycidic acid acyclic alkyl ester by step(s) under conditions such that an optically active 2-hydroxy-3-(4-alkyloxyphenyl)-3-(2-Aminophenylthio)propionic acid acyclic alkyl ester is prepared.

2. The process of claim 1, wherein the 2-Aminothiophenol is represented by the general formula:

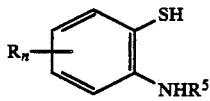

wherein the optically active 3-(4-alkyloxyphenyl)glycidic acid acyclic alkyl ester is represented by the general formula:

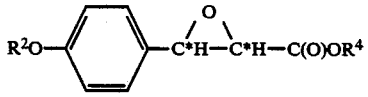

and wherein the optically active 2-hydroxy-3-(4alkyloxyphenyl)-3(2-Aminophenylthio)propionic acid acyclic alkyl ester is represented by the general formula:

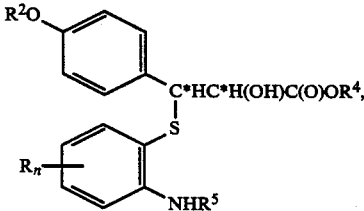

wherein:
n is an integer from 0 to 3;
R is separately at each occcurrence a halogen, lower alkyl, lower aklyloxy, lower aklylthio, lower aklanoloxy, hydroxy, benzyloxy, trifluoromethyl, nitro, cyano, or if n is 2 or more, a bridged alkyl group;
$R^2$ is lower alkyl;
$R^4$ is the acyclic alkyl, and
$R^5$ is hydrogen or lower alkyl, and wherein an optical activity component of net optical activity is due to the C* carbons.

3. The process of claim 2, wherein:
n is 0 or 1;
R is Cl, F, $CF_3$, $NO_2$, CN, methoxy, ethyl, or methyl;
$R^2$ is $C_{1-4}$ alkyl;
$R^4$ is $C_{1-4}$ alkyl, and
$R^5$ is hydrogen.

4. The process of claim 3, wherein the 2-Aminothiophenol is 2-aminothiophenol per se or 2-amino-5-chlorothiophenol.

5. The process of claim 1, 2, 3 or 4, conducted in the presence of a media of a $C_{7-8}$ aromatic hydrocarbon or a $C_{7-8}$ aryl-alkyl ether.

6. The process of claim 5, wherein the media contains toluene, a xylene or anisole.

7. The process of claim 6, wherein the media contains toluene.

8. The process of claim 5, wherein the optically active 2-hydroxy-3-(4-alkyloxyphenyl)-3-(2-Aminophenylthio)propionic acid acyclic alkyl ester is removed as a solid.

9. A process comprising contacting 2-aminothiophenol with a 3-(4-methoxyphenyl) glycidic acid methyl ester by step(s) in the presence of toluene at a temperature at least about 100° C. under conditions such that a 2-hydroxy-3-(4-methoxyphenyl)-3-(2-aminophenylthio)propionic acid methyl ester is prepared.

10. A process comprising contacting 2-aminothiophenol with a 3-(4-methoxyphenyl) glycidic acid methyl ester by step(s) in the presence of toluene at a temperature at least about 100° C under conditions such that a 2-hydroxy-3-(4-methoxyphenyl)-3-(2-aminophenylthio) propionic acid methyl ester is prepared, wherein said esters are optically active due to chirality of the 2- and 3- carbons of the glycidic and propionic acid chains.

11. The process of claim 10, wherein $(-)_{578}$-trans-3-(4-methoxyphenyl)glycidic acid methyl ester is employed, and $(+)_{578}$-threo(2S,3S)-2-hydroxy-3-(4-methoxyphenyl)-3-(2-aminophenylthio)propionic acid methyl ester is prepared.

12. The process of claim 9, 10 or 11, wherein the $(+)_{578}$-(2S,3S)-2-hydroxy-3-(4-methoxyphenyl)-3-(2-aminophenylthio)-propionic acid methyl ester is recovered as a solid.

13. The process of claim 1, wherein the optically active 2-hydroxy-3-(4-alkoxyphenyl)-3-(2-Aminophenylthio)propionic acid acyclic alkyl ester is substantially less soluble in a medium in which the process is carried out than corresponding racemic ester is soluble in.

14. The process of claim 1, wherein yield of the optically active 2-hydroxy-3-(4-alkoxyphenyl)-3-(2-Aminophenylthio) propionic acid acyclic alkyl ester is substantially higher than is yield of corresponding racemic ester as prepared by the otherwise same process.

* * * * *

REEXAMINATION CERTIFICATE (1716th)

United States Patent [19]

Martin

[11] B1 4,908,469

[45] Certificate Issued Jun. 2, 1992

[54] 2-HYDROXY-PROPANOIC ACID ACYCLIC ALKYL ESTERS FOR BENZOTHIAZEPINES

[75] Inventor: Daniel E. Martin, Lee's Summit, Mo.

[73] Assignee: Marion Laboratories, Inc., Kansas, Mo.

Reexamination Request:
No. 90/002,080, Jun. 26, 1990
No. 90/002,307, Mar. 26, 1991

Reexamination Certificate for:
Patent No.: 4,908,469
Issued: Mar. 13, 1990
Appl. No.: 195,709
Filed: May 18, 1988

[51] Int. Cl.$^5$ ............................................. C07D 281/10
[52] U.S. Cl. ................................. 360/17; 540/491; 549/549; 562/431
[58] Field of Search .................. 560/17; 562/431; 549/549; 540/491

[56] References Cited

FOREIGN PATENT DOCUMENTS 61-145159 7/1986 Japan .

*Primary Examiner*—Robert T. Bond

[57] ABSTRACT

In general, the present invention provides, in one aspect, a process comprising contacting a 2-Aminothiophenol with an optically active 3-(4-alkyloxyphenyl)glycidic acid acyclic alkyl ester by step(s) under conditions such that an optically active 2-hydroxy-3-(4-alkyloxyphenyl)-3-(2-Aminophenylthio)propionic acid acyclic alkyl ester is prepared. Another aspect comprises the optically active 2-hydroxy-3-(4-alkyloxyphenyl)-3-(2-Aminophenylthio)propionic acid acyclic alkyl ester. A preferred aspect is a process comprising contacting 2-aminothiophenol per se with a 3-(4-methoxyphenyl)glycidic acid methyl ester by step(s) under conditions such that a 2-hydroxy-3-(4-methoxyphenyl)-3-(2-aminophenylthio)propionic acid methyl ester is prepared.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-14 are cancelled.

* * * * *